United States Patent [19]

Flug et al.

[11] Patent Number: 5,401,275
[45] Date of Patent: Mar. 28, 1995

[54] APPARATUS FOR ENFORCING THE CLOSURE OF DIAPERING GARMENTS

[75] Inventors: Rachael Flug, Granada Hills; Jennifer Molinar, Agoura, both of Calif.

[73] Assignee: Diaperaps Limited, Chatsworth, Calif.

[21] Appl. No.: 757,811

[22] Filed: Sep. 11, 1991

[51] Int. Cl.$^6$ ............... A61F 13/15; A61F 13/20
[52] U.S. Cl. ................... 604/391; 604/358; 604/385.1; 604/386; 604/389
[58] Field of Search ............ 604/358, 385.1, 386, 604/391, 392, 389–390; 2/70, 111, 400

[56] References Cited

U.S. PATENT DOCUMENTS

| | | | |
|---|---|---|---|
| 2,477,914 | 8/1949 | Webb | 604/386 |
| 3,110,312 | 11/1963 | Wirth | 604/391 |
| 3,530,859 | 9/1970 | Heimowitz | 604/386 |
| 3,999,545 | 12/1976 | Milnamow | 604/390 |
| 4,581,772 | 4/1986 | Smith | 2/111 |
| 4,869,724 | 9/1989 | Scripps | 604/389 |
| 4,894,060 | 1/1990 | Nestegard | 604/391 |

FOREIGN PATENT DOCUMENTS

| | | | |
|---|---|---|---|
| 679196 | 2/1964 | Canada | 604/391 |
| 2195230 | 4/1988 | United Kingdom | 2/400 |

*Primary Examiner*—Randall L. Green
*Assistant Examiner*—P. Zuttarelli
*Attorney, Agent, or Firm*—Thomas I. Rozsa; Tony D. Chen

[57] ABSTRACT

The present invention is a closure enforcing apparatus for diapering garments. The diapering garment has a main piece with a contoured edge. There is at least one primary fastener fully attached to the main piece near the contoured edge, and at least one complementary fastener fully attached to the main piece also near the contoured edge but at a remote location, such that the primary fastener can be mated onto the complementary fastener to close the diapering garment. In addition, there is at least one secondary fastener being the same type as the primary fastener, and having a free floating end laterally extending out from the contoured edge of the main piece and an opposite end attached to the main piece near the primary fastener. The size of the complementary fastener is substantially smaller than that of the primary fastener, and the thickness of the secondary fastener is substantially thinner than that of the contoured edge of the main piece. As the primary fastener is mated onto the complementary fastener, the secondary fastener can also be mated onto the complementary fastener to enforce the closure of the diapering garment.

35 Claims, 4 Drawing Sheets

FIG.7
(Section on line 7 - 7)

APPARATUS FOR ENFORCING THE CLOSURE OF DIAPERING GARMENTS

BACKGROUND OF THE INVENTION

1. Field of the Invention

The present invention relates to the field of diapering garments, such as diapers, diaper covers, the combinations of a diaper and diaper cover, and diapering pants. More particularly, the present invention relates to the field of the closing mechanism of diapering garments.

2. Description of the Prior Art

Many types of diapering garments on the market today, whether designed and manufactured for commercial use or home use, utilize VELCRO-R fasteners for fastening purposes. There are two complementary types of VELCRO-R fasteners: male fasteners and female fasteners. Typically, each VELCRO-R fastener includes a thin backing which has two opposite surfaces: a front surface and a back surface. The back surface of a VELCRO-R fastener usually has no functional structures: the functional structure of the VELCRO-R fastener is carried on its front surface. The front surface of a male fastener is a hook type mating surface which has a large amount of filamentary hook members. The front surface of a female fastener is a loop type mating surface which has a large amount of filamentary loop members. When the hook type mating surface of a male fastener is pressed onto the loop type mating surface of a female fastener, the filamentary hook members of the male fastener will fasten onto the filamentary loop members of the female fastener, to thereby fasten the two fasteners together.

Figures 1, 2, 3, 4:
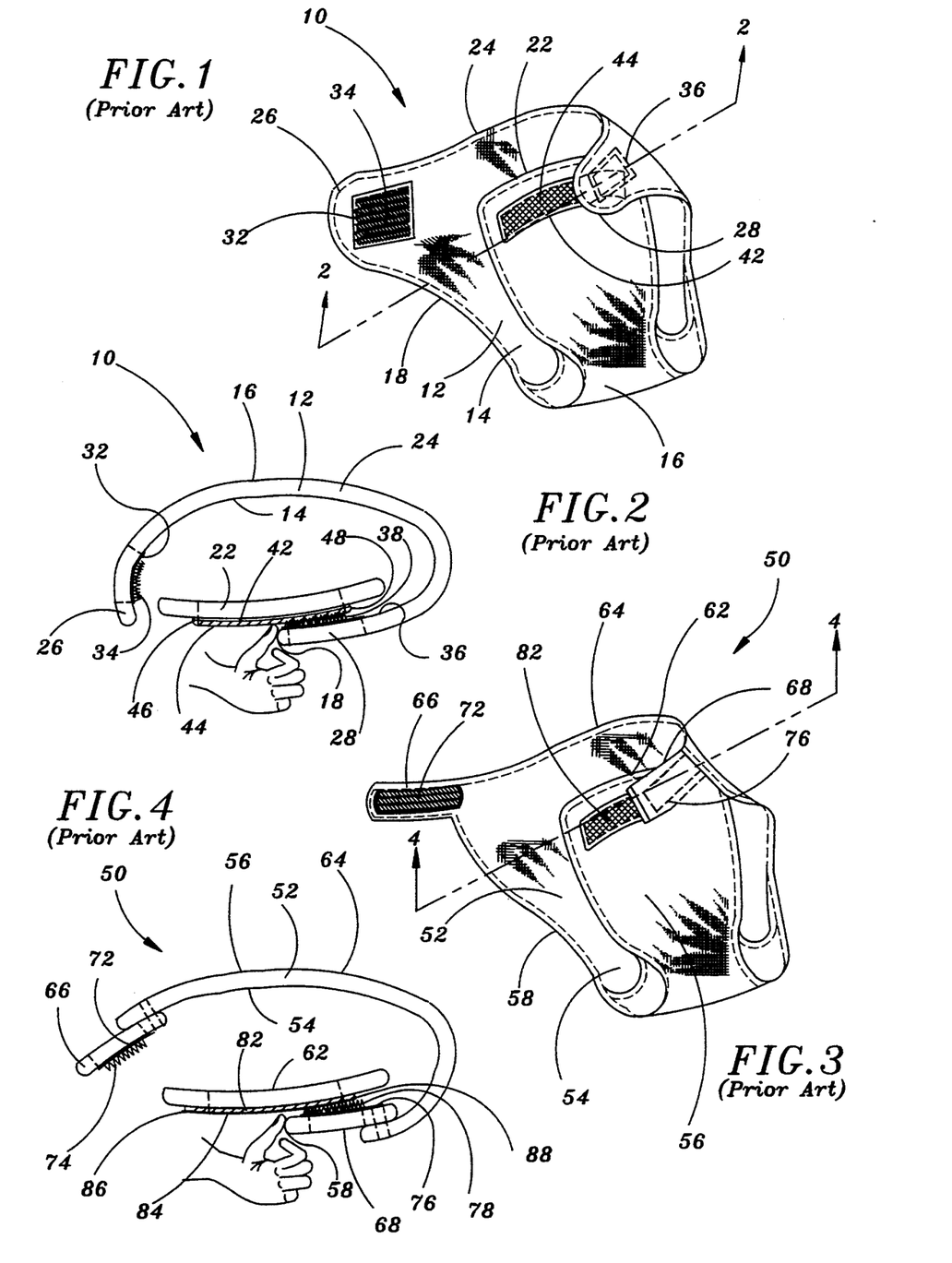
FIG. 1 is a perspective view of a prior art diapering garment.
FIG. 2 is a cross-sectional view taken along line 2—2 of FIG. 1.
FIG. 3 is a perspective view of another prior art diapering garment.
FIG. 4 is a cross-sectional view taken along line 4—4 of FIG. 3.

Referring to FIG. 1, there is shown a prior art diapering garment 10, which represents a typical structure of currently available diapering garments. This prior art diapering garment 10 has an hourglass shaped main piece 12, which has an interior surface 14, an exterior surface 16 and a circumferential edge 18. The main piece 12 of the diapering garment 10 also has a generally straight front end 22, and a widened rear end 24 that extends to two arcuate shaped rear corners 26 and 28.

A first male VELCRO-R fastener 32 is affixed on the interior surface 14 of the diapering garment 10 at the first rear corner 26, adjacent to the circumferential edge 18. The hook type mating surface 34 of the first male fastener 32 is facing away from the interior surface 14 of the diapering garment 10. A second male fastener 36 is also affixed on the interior surface 14 of the diapering garment 10 at the second rear corner 28, adjacent to the circumferential edge 18. The hook type mating surface 38 of the second male fastener 36 is again facing away from the interior surface 14 of the diapering garment 10.

An elongated female fastener 42 is affixed on the exterior surface 16 of the diapering garment 10 at the straight front end 22, also adjacent to the circumferential edge 18. The loop type mating surface 44 of the female fastener 42 is facing away from the exterior surface 16 of the diapering garment 10. The elongated female fastener 42 has a first end 46 and a second end 48. When the diapering garment 10 is fastened onto a baby, its front end 22 is positioned adjacent to the baby's stomach, its rear end 24 is positioned adjacent to the baby's buttocks, and its two rear corners 26 and 28 are wrapped respectively around the opposite sides of the baby's waist from back to front. The first male fastener 32 can be affixed onto the first end 46 of the elongated female fastener 42, and the second male fastener 36 can be affixed onto the second end 48 of the elongated female fastener 42, to thereby fasten the diapering garment 10 onto the baby.

A special problem has been experienced by parents who use this type of diapering garment for their babies. The problem is that babies like to play with the fasteners. Referring to FIG. 2, there is shown as an example the attachment of the second rear corner 28 and the front end 22. When the hook type mating surface 38 of the second male fastener 36 is affixed onto the loop type mating surface 44 of the female fastener 42, many babies like to stick their little thumbs or fingers under the relatively heavy and thick edge 18 of the second rear corner 28, which provides an ideal object for the babies' thumbs or fingers to grasp or lift. It is understood that the heaviness and thickness of the corner portions of the diapering garment mentioned here and hereafter are relative as compared to the heaviness and thickness of the small and thin backing piece of the male and female VELCRO-R fasteners. This gives the babies something to play with. It has also been found that babies like to hear the sound generated by separating the VELCRO-R fasteners, as they are lifting the relatively heavy and thick edge of the rear corners from the front end of the diapering garment. With enough dexterity, babies often can fully open the male and female fasteners. As a result, the respective rear corner is completely detached from the front end of the diapering garment, and the diapering garment will fall off. This is very undesirable for parents because the loosened diapering garment enables the baby's excrement to flow and fall out of the diapering garment.

The same problem has also been experienced by parents who use another type of currently available prior art diapering garment for their babies, which is represented by the diapering garment shown in FIG. 3 at 50. Prior art diapering garment 50 is similar to the prior art diapering garment 10 shown in FIG. 1, except at its rear corners.

As shown in FIG. 3, the prior art diapering garment 50 has an elongated main piece 52, which has an interior surface 54, an exterior surface 56 and a circumferential edge 58. The main piece 52 of the diapering garment 50 also has a generally straight front end 62, and a generally straight rear end 64. Unlike the other prior art diapering garment 10, the main piece 52 of this diapering garment 50 does not have two arcuate shaped rear corners. Instead, it has two corner bands 66 and 68 laterally extended from and oppositely disposed at the rear end 64 of the diapering garment 50. One end of each corner band is attached to the edge 58 of the diapering garment 50, and the other opposite end is free floating. Each corner band also has an interior surface which merges with the interior surface 54 of the diapering garment 50, and an exterior surface which merges with the exterior surface 56 of the diapering garment 50.

Referring to FIG. 4, a first male VELCRO-R fastener 72 is affixed on the interior surface of the first corner band 66. The hook type mating surface 74 of the first male fastener 72 is facing away from the interior surface of first corner band 66. A second male fastener 76 is affixed on the interior surface of the second corner band 68. The hook type mating surface 78 of the second male fastener 76 is facing away from the interior surface of the second corner band 68.

An elongated female fastener 82 is affixed on the exterior surface 56 of the diapering garment 50 at the straight front end 62, also adjacent to the circumferential edge 58. The loop type mating surface 84 of the female fastener 82 is facing away from the exterior surface 56 of the diapering garment 50. The elongated female fastener 82 also has a first end 86 and a second end 88. When the diapering garment 50 is fastened onto a baby, its front end 62 is positioned adjacent to the baby's stomach, its rear end 64 is positioned adjacent to the baby's buttocks, and its two corner bands 66 and 68 are wrapped respectively around the opposite sides of the baby's waist from back to front. The first male fastener 72 can be affixed onto the first end 86 of the elongated female fastener 82, and the second male fastener 76 can be affixed onto the second end 88 of the elongated female fastener 82, to thereby fasten the diapering garment 50 onto the baby.

The problem with this type of diapering garment is again, for example, that the relatively heavy and thick corner band 68 provides an ideal object for babies to play with. Babies like to stick their little thumbs or fingers under the relatively heavy and thick corner band 68, as shown in FIG. 4, and pull the male and female fasteners open.

It is desirable to have an apparatus which enforces the closure mechanism of the diapering garments so that babies will have a more difficult time in opening the diapering garments.

SUMMARY OF THE INVENTION

The present invention is an apparatus for enforcing the closure of diapering garments.

It is known that VELCRO-R type male and female fasteners are widely utilized in diapering garments such as diapers, diaper covers, the combinations of a diaper and diaper cover, and diapering pants. One problem found in using these kinds of diapering garments is that, since the male or female fasteners are often affixed onto and fully supported by a relatively heavy and thick piece of fabric such as the corners or corner bands of the diapering garments, babies can stick their thumbs or fingers under the edge of the relatively heavy and thick piece of fabric backing the male or female fasteners and try to pull them open. Sometimes the babies can completely lift up the fabric pieces supporting the male or female fasteners, and therefore cause the diapering garments to fall off.

It has been discovered, according to the present invention, that while the relatively heavy and thick edges of the corners or corner bands of the diapering garments present a problem as described above, it is still necessary to fully attach the male or female fasteners to those relatively heavy and thick corners or corner bands of the diapering garments, to sustain the strength applied on the male or female fasteners when the diapering garments are closed. Therefore, the original arrangement of the male and female fasteners should be retained. However, to prevent the problem as described above, in addition to these original male or female fasteners which may be considered as primary fasteners, a new set of male or female fasteners may be provided in conjunction with the primary fasteners. In addition, although one could use snaps on a diapering garment as fasteners, the snaps do not provide the desired adjustability. The male hook type and female loop type fasteners provide maximum adjustability.

It is therefore an object of the present invention to provide an apparatus for enforcing the closure of the diapering garments. The enforcement apparatus includes a new set of male or female fasteners, which may be considered as secondary fasteners. The secondary fasteners are located adjacent to the primary fasteners respectively, and extend out from the relatively heavy and thick edges of the corners or corner bands of the diapering garments. They are not supported by any additional pieces other than their own small and thin backings. When they are affixed on the complementary fasteners, babies are unable to pull them up because they do not have relatively heavy and thick edges into which the babies can stick their thumbs or fingers. Therefore the secondary fasteners provide a double-closing mechanism for the primary fasteners, which prevents the babies from completely opening up the diapering garments.

It is an additional object of the present invention to provide an apparatus for enforcing the closure of the diapering garments which is safe for the babies. Since the secondary fasteners are nondetachably attached to the diapering garments, there are no loose parts which the babies can put into their mouths.

It is a further object of the present invention to provide an apparatus for enforcing the closure of the diapering garments which is cost efficient to manufacture. Since the secondary fasteners are small pieces of VELCRO-R male or female fasteners directly attached to the diapering garments without any additional supporting piece, the cost of manufacturing the diapering garments will not be significantly increased.

It is also an object of the present invention to provide an apparatus for enforcing the closure of the diapering garments which utilizes male hook type and female loop type fasteners since they provide maximum adjustability for different sized babies, thereby assuring a tight and comfortable fit.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figures 5, 6, 7:
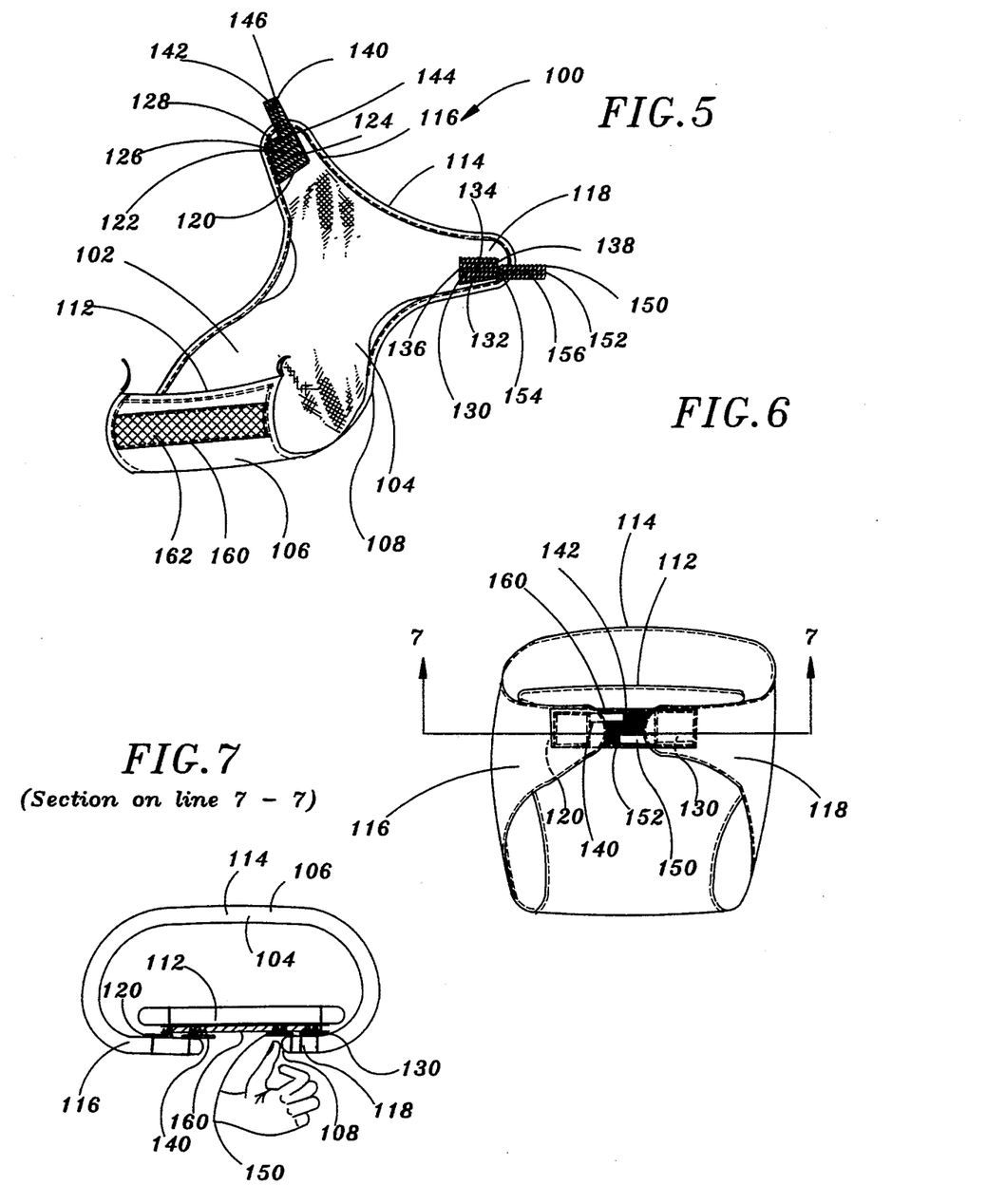
FIG. 5 is a perspective view of a preferred embodiment of the present invention diapering garment having closure enforcing apparatus in its fully opened position.
FIG. 6 is a perspective view of the preferred embodiment of the present invention diapering garment having closure enforcing apparatus in its fully closed position.
FIG. 7 is a cross-sectional view taken along line 7—7 of FIG. 6.

Referring to FIG. 5, there is shown at 100 one of the preferred embodiments of the present invention diapering garment. The diapering garment may be a diaper or a diaper cover for babies or a diapering pant for adults. The diapering garment has a main diapering piece 102. The main diapering piece 102 may have an hourglass shape or any other suitable shape. It may have a single layer construction or a multi-layer construction. It may be made of fabric material or any other suitable material, or any suitable combinations of materials. It may have the characteristic properties such as soft and flexible, elastic, stretchable, air pervious and liquid impervious or liquid absorptive, or any other suitable characteristic property. In addition to the main diapering piece 102, the present invention diapering garment 100 may further comprise other additional functional pieces, such as two small gussets at the crotch area of the diapering garment 100.

In the preferred embodiments of the present invention, the main diapering piece 102 is hourglass shaped. Generally, the main diapering piece 102 has an interior surface 104, an exterior surface 106 and a circumferential edge 108. The main diapering piece 102 further has a generally straight front end 112 and a widened rear end 114. Preferably, the widened rear end 114 is expanding laterally to form two oppositely disposed and arcuate shaped rear corners 116 and 118.

One of the unique features of the present invention is to provide two sets of fasteners to securely close the diapering garment 100. The first set of fasteners includes two primary male fasteners 120 and 130. The primary male fasteners 120 and 130 may have rectangular or square shaped configurations, or arcuate shaped configurations, or any other suitable configuration. In the preferred embodiments of the present invention, they are generally square shaped.

The first primary male fastener 120 is fully stitched onto the interior surface 104 of the first corner 116 of the main diapering piece 102 adjacent to the circumferential edge 108, such that its hook type mating surface 122 is facing away from the interior surface 104 of the main diapering piece 102. The first primary male fastener 120 has an upper half portion 124 adjacent to the rear end 114 of the main diapering piece 102, and an opposite lower half portion 126. The outer edge 128 of the square shaped first primary male fastener 120 is adjacent to the circumferential edge 108 of the main diapering piece 102.

The second primary male fastener 130 is fully stitched onto the interior surface 104 of the second corner 118 of the main diapering piece 102 adjacent to the circumferential edge 108, such that its hook type mating surface 132 is facing away from the interior surface 104 of the main diapering piece 102. The second primary male fastener 130 also has an upper half portion 134 adjacent to the rear end 114 of the main diapering piece 102, and an opposite lower half portion 136. The outer edge 138 of the square shaped second primary male fastener 130 is also adjacent to the circumferential edge 108 of the main diapering piece 102.

The second set of fasteners includes two secondary male fasteners 140 and 150. The secondary male fasteners 140 and 150 may have rectangular or square shaped configurations, or arcuate shaped configurations, or any other suitable configuration. In the preferred embodiments of the present invention, they are generally rectangular shaped. In addition, the size of each secondary male fastener is preferably less than or about half of the size of each primary male fastener.

The first secondary male fastener 140 has a free floating outer end 142 extended from the circumferential edge 108 of the main diapering piece 102, and an opposite inner end 144 attached to the first rear corner 116 of the main diapering piece 102 adjacent to the first primary male fastener 120, such that its hook type mating surface 146 is facing the same direction as the hook type mating surface 122 of the first primary male fastener 120.

The second secondary male fastener 150 also has a free floating outer end 152 extended from the circumferential edge 108 of the main diapering piece 102, and an opposite inner end 154 attached to the second rear corner 118 of the main diapering piece 102 adjacent to the second primary male fastener 130, such that its hook type mating surface 156 is facing the same direction as the hook type mating surface 132 of the first primary male fastener 130.

The two primary male fasteners 120 and 130 and the two secondary male fasteners 140 and 150 are all mated onto one female fastener 160. The female fastener 160 is generally rectangular shaped. It is fully stitched onto the exterior surface 106 of the main diapering piece 102 adjacent to the straight front end 112, such that its loop type mating surface 162 is facing away from the exterior surface 106 of the main diapering piece 102. Preferably, the length of the female fastener 160 is extended along the entire front end 112 of the main diapering piece 102.

In the preferred embodiments of the present invention, the two primary and two secondary male fasteners are made of male VELCRO-R fasteners, and the elongated female fastener is made of female VELCRO-R fastener. As mentioned earlier, each VELCRO-R fastener has a thin backing which has a front surface and an opposite back surface. There are usually no functional structures on the back surface of a VELCRO-R fastener. The functional mating surface of the VELCRO-R fastener is carried on its front surface. The front surface of a male fastener is a hook type mating surface which has a large amount of filamentary hook members, and the front surface of a female fastener is a loop type mating surface which has a large amount of filamentary loop members. When the male and female VELCRO-R fasteners are attached to the main diapering piece 102, it is their non-functional back surfaces which are brought into contact with the main diapering piece 102. One of the preferred methods of attachment is stitching. The stitching lines stitch the thin backing of each VELCRO-R fastener onto the designated surface of the main diapering piece 102.

The main diapering piece can be closed, as shown in FIG. 6, by affixing the two primary male fasteners 120 and 130 onto the elongated female fastener 160. Now, as a unique feature of the enforced closing mechanism of the present invention, the two secondary male fasteners 140 and 150 are also affixed onto the elongated female fastener 160. Described in detail, the free floating outer end 142 of the first secondary male fastener 140 is now closed onto the elongated female fastener 160 to enforce the closure of the first primary male fastener 120, and the free floating outer end 152 of the second secondary male fastener 150 is now closed onto the elongated female fastener 160 to enforce the closure of the second primary male fastener 130. The two secondary male fasteners 140 and 150 are affixed onto the elongated female fastener 160 between the two primary male fasteners 120 and 130. Referring to FIG. 7, shown as an example, now although a baby can still stick his or her thumb or fingers under the relatively heavy and thick edge 108 of the second rear corner 118 of the main diapering piece 102, he or she cannot open the second primary male fastener 130 from the elongated female fastener 160 because of the closing enforcement provided by the second secondary male fastener 150. Instead, this gives babies something more interesting to play with for a longer period of time, because babies can keep trying to open and playing with the two primary male fasteners 120 and 130.

On the other hand, babies cannot open the two secondary male fasteners 140 and 150, because the backings of the two secondary male fasteners 140 and 150 are so thin that the babies' thumbs or fingers are unable to stick under or grasp them. For example, the thickness of the circumferential edge of a typical diapering garment is no less than a quarter of an inch (¼"), but the thickness of the backing of a VELCRO-R male fastener is less than a hundredth of an inch (1/100"). Since the thickness and heaviness of the two secondary male fasteners 140 and 150 are substantially less than those of the circumferential edge of the main diapering piece 102, the babies cannot open the two secondary male fasteners 140 and 150 by sticking their thumbs or fingers under them and lifting them. This double closing mechanism provided by the second set of fasteners can successfully enforce the closure of the primary fasteners and prevent the diapering garment from undesirably falling off.

The present invention closure enforcement apparatus is designed to be safe and comfortable for the babies. It utilize the same VELCRO-R fasteners which are soft and flexible. The two added secondary male fasteners 140 and 150 are securely attached to the main diapering piece, so that there is nothing loose that can be pulled off for the babies to put in their mouths.

The present invention closure enforcement apparatus is also constructed cost efficiently. Only two small pieces of secondary male VELCRO-R fasteners are added, and they share the same female VELCRO-R fasteners with the two primary male VELCRO-R fasteners. There is no other closing member added, such as a flap, strap, band or buckle. In addition, although snaps or the like fasteners could be used on a diapering garment, they do not provide the desired adjustability as the male hook type and female loop type fasteners do. Utilizing the male hook type and female loop type fasteners can provide maximum adjustability to a diapering garment.

The present invention closure enforcement apparatus is also made to be adaptable with an adjustable diapering garment. When the main diapering piece 102 is worn by a newborn baby, the fitness of the main diapering piece 102 is usually adjusted by affixing the two primary male fasteners 120 and 130 closer to each other. Since the two secondary male fasteners 140 and 150 are disposed between the two primary male fasteners 120 and 130, they are offset to avoid having their outer ends 142 and 152 overlapped onto each other. Referring to FIGS. 5 and 6, the first secondary male fastener 140 is aligned with the upper half portion 124 of the first primary male fastener 120, and the second secondary male fastener 150 is aligned with the lower half portion 134 of the second primary male fastener 130. This special arrangement is designed for right-handed babies. When the main diapering piece 102 is worn on a baby, the first rear corner 116, the first primary male fastener 120 and the first secondary male fastener 140 are located on the right side of the baby, and the second rear corner 118, the second primary male fastener 130 and the second secondary male fastener 150 are located on the left side of the baby (although they may appear oppositely in the figures). A right-handed baby is more like to grasp the lower portion of the first (right) rear corner 116. Having a secondary male fastener 140 located at the upper right portion makes it more difficult for the right-handed baby to open the first (right) rear corner 116. Since a majority of babies turn out to be right-handed, in the preferred embodiment the first (right) secondary male fastener 140 is aligned with the upper half portion 124 of the first (right) primary male fastener 120 at the first (right) rear corner 116, and the second (left) secondary male fastener 150 is aligned with the lower half portion 134 of the second (left) primary male fastener 130 at the second (left) rear corner 118.

Figure 8:
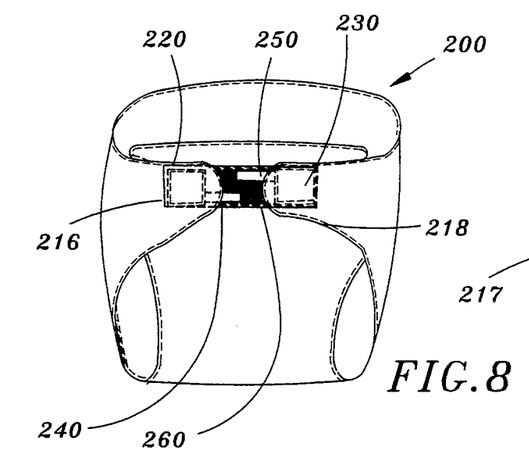
FIG. 8 is a perspective view of one of the alternative embodiments of the present invention diapering garment having closure enforcing apparatus in its fully closed position.

Of course this arrangement can be modified to suit a left-handed baby. As shown in FIG. 8, in an alternative embodiment of the present invention diapering garment 200, the first (right) secondary male fastener 240 is lower down at the first (right) rear corner 216, and the second (left) secondary male fastener 250 is higher up at the second (left) rear corner 218, so that it is more difficult for the left-handed baby to open the second (left) rear corner 218.

In addition to being designed for right-handed and left-handed babies, the offset feature of the two secondary enforcing male fasteners is also designed for making the enforcement closure apparatus more difficult for babies to open, because the babies require more coordination with their hands to open the offset secondary fasteners.

Figure 9:
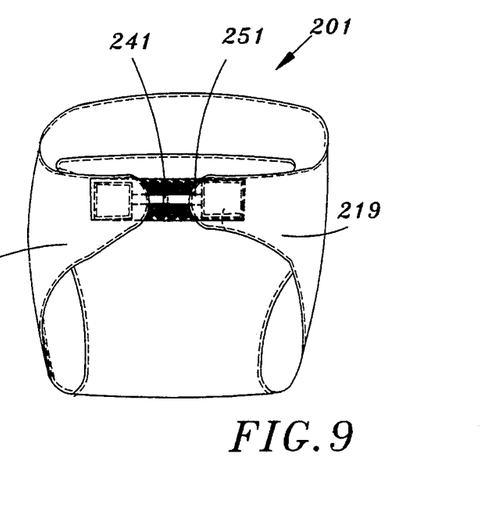
FIG. 9 is a perspective view of another one of the alternative embodiments of the present invention diapering garment having closure enforcing apparatus in its fully closed position.

Moreover, the two secondary male fasteners may not be completely but partially offset, or they may be aligned with each other. As shown in FIG. 9, in another alternative embodiment of the present invention diapering garment 201, the first (right) secondary male fastener 241 at the first (right) rear corner 217 is aligned with the second (left) secondary male fastener 251 at the second (left) rear corner 219, although when worn by a small baby the two secondary male fasteners may partially overlap each other.

The various detailed arrangements of the attachment of the secondary male fasteners are shown in FIGS. 10 through 14. As an example, only the attachment at the second arcuate shaped rear corner 118 of the main diapering piece is shown.

Figures 10, 11, 12, 13, 14:
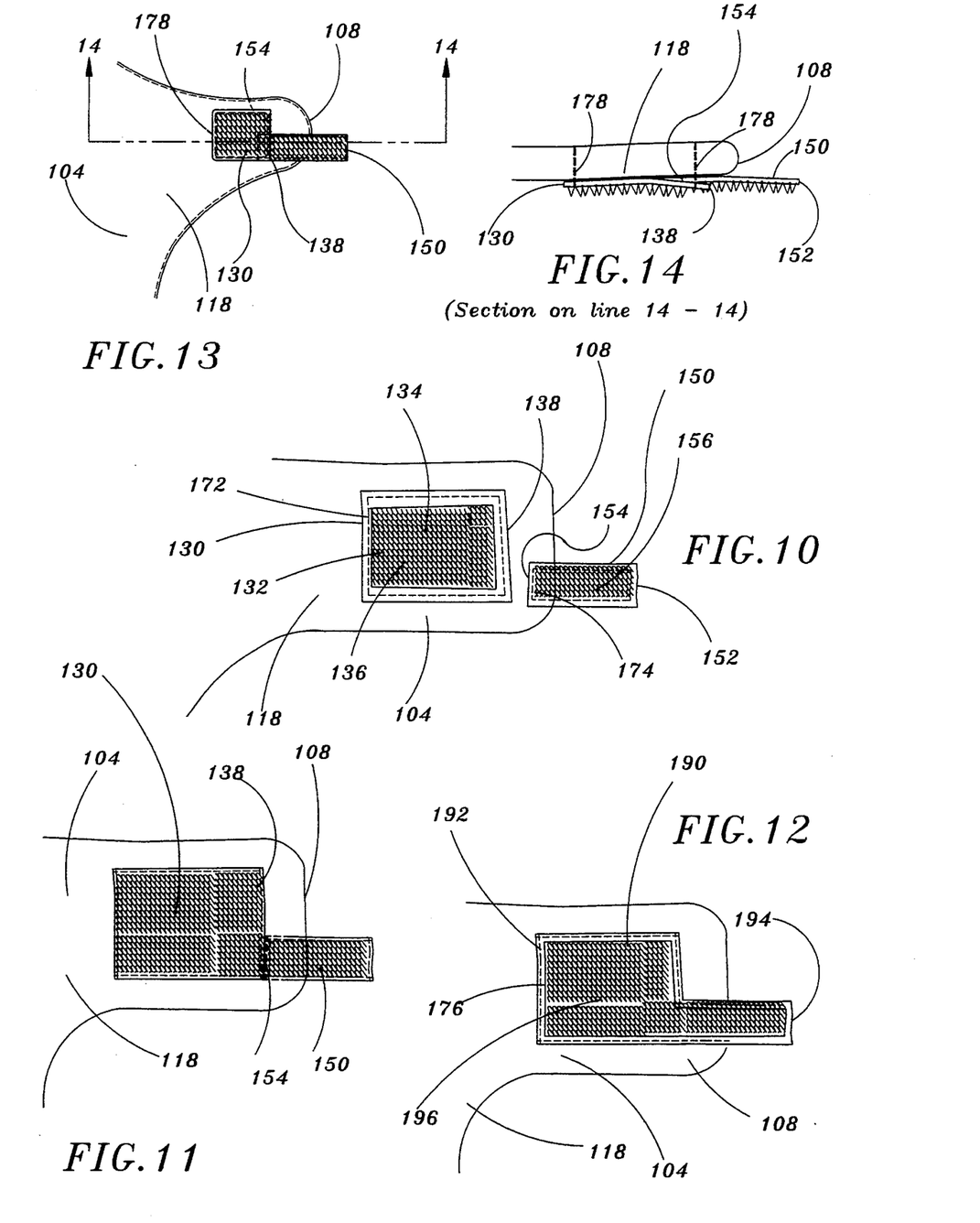
FIG. 10 is a partial view of a rear corner part of a diapering garment showing one embodiment of the closure enforcing apparatus of the present invention.
FIG. 11 is a partial view of a rear corner part of a diapering garment showing another embodiment of the closure enforcing apparatus of the present invention.
FIG. 12 is a partial view of a rear corner part of a diapering garment showing an alternative embodiment of the closure enforcing apparatus of the present invention.
FIG. 13 is a partial view of a rear corner part of a diapering garment showing one preferred embodiment of the closure enforcing apparatus of the present invention.
FIG. 14 is a cross-sectional view taken along line 14—14 of FIG. 13.

The general attachment is shown in FIG. 10. The second primary male fastener 130 is generally square shaped. It is fully affixed onto the interior surface 104 of the second rear corner 118 adjacent to the circumferential edge 108 by square shaped stitching pattern 172. Its hook type mating surface 132 is exposed and facing away from the interior surface 104. The outer end 152 of the second secondary male fastener 150 is free floating and extending laterally from the circumferential edge 108. The opposite inner end 154 of the second secondary male fastener 150 is affixed onto the interior surface 104 of the second rear corner 118 between the circumferential edge 108 and the outer edge 138 of the second primary male fastener 130 by a single stitching line 174. The second secondary male fastener 150 is aligned with the lower half portion 136 of the second primary male fastener 130, and its hook type mating surface 156 is facing the same direction as the hook type mating surface 132 of the second primary male fastener 130.

The inner end 154 of the second secondary male fastener 150 may be located immediately next to the outer edge 138 of the second primary male fastener 130, such as the particular arrangement shown in FIG. 11. Moreover, the pair of connected primary and secondary male fasteners can be integrally formed by a unitary piece of generally L-shaped male VELCRO-R fastener 190, such as shown in FIG. 12. This generally L-shaped VELCRO-R male fastener 190 may be affixed onto the interior surface 104 of the second rear corner 118 adjacent to the circumferential edge 108 by a suitable stitching pattern 176. Its large wide portion 192 will be located within the second rear corner 118, but its small narrow portion 194 will be free floating and extending out from the circumferential edge 108. Its hook type mating surface 196 is exposed and facing away from the interior surface 104.

In another preferred embodiment, the inner end 154 of the second secondary male fastener 150 is located underneath the outer edge 138 of the second primary male fastener 130, and the two male fasteners 130 and 150 are stitched by a single square shaped stitching pattern 178, such as shown in FIGS. 13 and 14. In other words, the separate stitching line 174 for attaching the second secondary male fastener 150 is eliminated. This makes the manufacturing of the present invention diapering garment more cost efficient.

Figures 15, 16, 17:
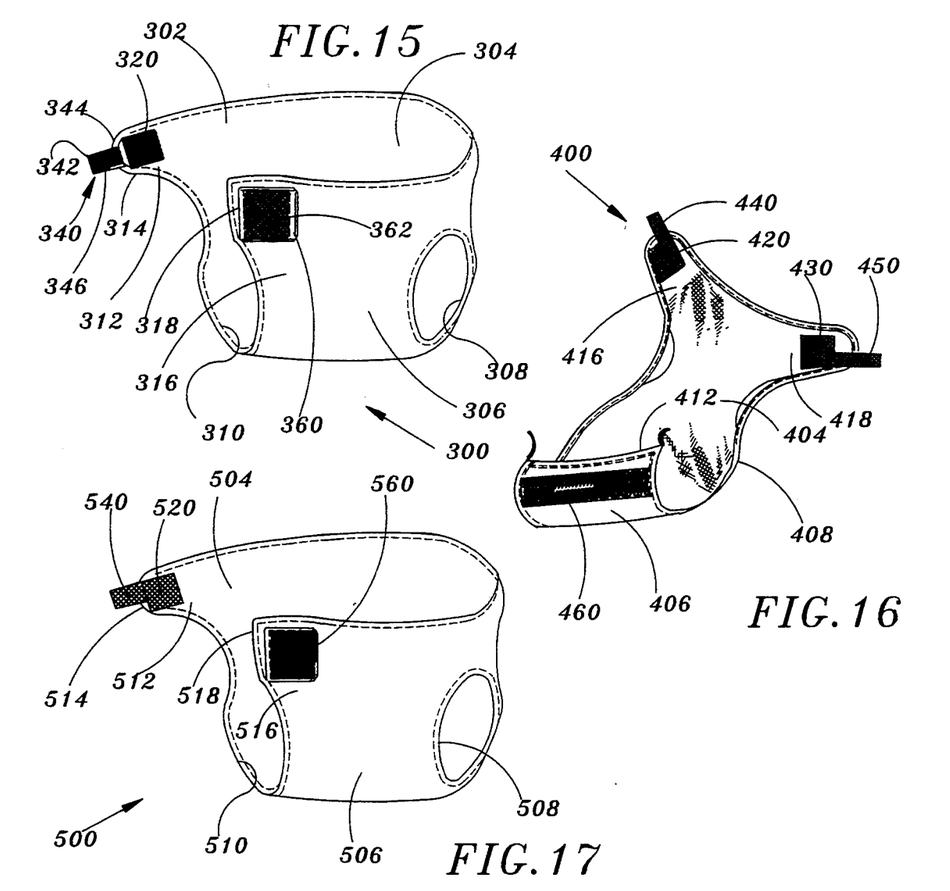
FIG. 15 is a perspective view of still another alternative embodiment of the present invention diapering garment having closure enforcing apparatus in its opened position.
FIG. 16 is a perspective view of a further alternative embodiment of the present invention diapering garment having closure enforcing apparatus in its opened position.
FIG. 17 is a perspective view of an additional alternative embodiment of the present invention diapering garment having closure enforcing apparatus in its opened position.

The diapering garments so far discussed are more oriented toward the diapers and diaper covers for newborn or young babies, particularly the most popular hourglass shaped diapers and diaper covers. However, the principle of the double closure enforcement apparatus can be applied to various other types of diapering garments. As an example, there is shown in FIG. 15 side-opening diapering pants 300 for adults, which utilize the double closure enforcement apparatus of the present invention.

The diapering pant 300 has a main diapering piece 302 which has an interior surface 304 and an exterior surface 306. The main diapering piece 302 further has a closed side opening 308 for allowing a user to insert one leg and an opposite split side opening 310 defined by the edge 314 of a first side panel 312 and the edge 318 of a second side panel 316. A primary male fastener 320 is fully stitched onto the interior surface 304 of the main diapering piece 302 and located adjacent to the edge 314 of the first side panel 312, such that its hook type mating surface 322 is facing away from the interior surface 304 of the main diapering piece 302. A secondary male fastener 340 has a free floating outer end 342 laterally extended from the edge 314 of the first side panel 312, and an opposite inner end 344 stitched to interior surface 304 of the first side panel 312 at a location adjacent to the primary male fastener 320, such that its hook type mating surface 346 is facing the same direction as the hook type mating surface 322 of the primary male fastener 320. A female fastener 360 is fully stitched onto the exterior surface 306 of the main diapering piece 302 and located adjacent to the edge 318 of the second side panel 316, such that its loop type mating surface 362 is facing away from the exterior surface 306 of the main diapering piece 302. The size of the secondary male fastener 340 is about half of the size of the primary male fastener 320, and the size of the female fastener 360 is about twice the size of the primary male fastener 320. Again, the secondary male fastener 340 is substantially thinner than the edge 314 of the first side panel 312. When the primary male fastener 320 is closed onto the female fastener 360 to close the diapering garment 300, the secondary male fastener 340 can also be closed onto the female fastener 360 to enforce the closure of the primary male fastener 320.

It will be appreciated that the male fasteners and the female fasteners of the present invention may be reversed to form other alternative embodiments of the present invention. For example, the male type and female type of the fasteners of the diapering garment 100 may be reversed to form an alternative diapering garment 400 shown in FIG. 16, where the two primary fasteners 420 and 430, and the two secondary fasteners 440 and 450 attached on the interior surface 404 and located respectively adjacent to the two rear corners 416 and 418 are all female VELCRO-R fasteners, and the elongated fastener 460 attached onto the exterior surface 406 and located adjacent to the front end 412 is a male VELCRO-R fastener. Another example is the diapering pant 500 shown in FIG. 17, which is a modification of the diapering pant 300 shown in FIG. 15 with reversed male and female fasteners, where the primary fastener 520 and the secondary fastener 540 attached on the interior surface 504 and located adjacent to the edge 514 of the first side panel 512 are female VELCRO-R fasteners, and the enlarged fastener 560 attached onto the exterior surface 506 and located adjacent to the edge 518 of the second side panel 516 is a male VELCRO-R fastener.

Another obvious variation of the present invention is to alter the attaching surfaces of the VELCRO-R fasteners. For example, the two primary and two secondary male fasteners on the diapering garment 100 shown in FIG. 1 may be attached to the exterior surface 106 of the main diapering piece 102, and the elongated female fastener may be attached to the interior surface 104 of the main diapering piece 102 correspondingly. A further variation is to provide two separate shortened female fasteners to replace the elongated female fastener 160 of the diapering garment 100. Moreover, the female fasteners of the present invention diapering garment may have either loop type mating surfaces or brushed nylon type mating surfaces.

Defined in detail, the present invention is a diapering garment, comprising: (a) a generally hourglass shaped main diapering piece having an interior surface, an exterior surface and a circumferential edge; (b) said main diapering piece further having a generally straight front end and a widened rear end with two arcuate shaped rear corners; (c) two primary male fasteners fully attached onto said interior surface of said main diapering piece, and respectively located at said two rear corners adjacent to said circumferential edge of said main diapering piece, such that their hook type mating surfaces are facing away from said interior surface of said main diapering piece; (d) an elongated female fastener fully attached onto said exterior surface of said main diapering piece, and located at said front end adjacent to said circumferential edge of said main diapering piece, such that its loop type mating surfaces are facing away from said exterior surface of said main diapering piece; (e) two secondary male fasteners each having a free floating outer end laterally extended from said circumferential edge of said main diapering piece, and an opposite inner end attached to said main diapering piece at a location adjacent to a respective one of said two primary male fasteners respectively, such that the hook type mating surfaces of the two secondary male fasteners are facing the same direction as the hook type mating surfaces of said two primary male fasteners; and (f) said two secondary male fasteners being substantially thinner than said circumferential edge of said main diapering piece; (g) whereby when said two primary male fasteners are closed onto said elongated female fastener to close said diapering garment, said two secondary male fasteners can also be closed onto said elongated female fastener to enforce the closure of said two primary male fasteners.

Defined alternatively, the present invention is a diapering garment, comprising: (a) a generally hourglass shaped main diapering piece having an interior surface, an exterior surface and a circumferential edge; (b) said main diapering piece further having a generally straight front end and a widened rear end with two arcuate shaped rear corners; (c) two primary female fasteners fully attached onto said interior surface of said main diapering piece, and respectively located at said two rear corners adjacent to said circumferential edge of said main diapering piece, such that their loop type mating surfaces are facing away from said interior surface of said main diapering piece; (d) an elongated male fastener fully attached onto said exterior surface of said main diapering piece, and located at said front end adjacent to said circumferential edge of said main diapering piece, such that its hook type mating surfaces are facing away from said exterior surface of said main diapering piece; (e) two secondary female fasteners each having a free floating outer end laterally extended from said circumferential edge of said main diapering piece, and an opposite inner end attached to said main diapering piece at a location adjacent to a respective one of said two primary female fasteners respectively, such that the loop type mating surfaces of the two secondary female fasteners are facing the same directions as the loop type mating surfaces of said two primary female fasteners; and (f) said two secondary female fasteners being substantially thinner than said circumferential edge of said main diapering piece; (g) whereby when said two primary female fasteners are closed onto said elongated male fastener to close said diapering garment, said two secondary female fasteners can also be closed onto said elongated male fastener to enforce the closure of said two primary female fasteners.

Defined also alternatively, the present invention is a diapering garment, comprising: (a) a main diapering piece having an interior surface and an exterior surface; (b) said main diapering piece further having a closed side opening, and an opposite split side opening defined by the edges of a first and a second side panels; (c) at least one primary male fastener fully attached onto said interior surface of said main diapering piece, and located adjacent to said edge of said first side panel, such that its hook type mating surface is facing away from said interior surface of said main diapering piece; (d) at least one female fastener fully attached onto said exterior surface of said main diapering piece, and located adjacent to said edge of said second side panel, such that its loop type mating surface is facing away from said exterior surface of said main diapering piece; (e) the size of said at least one female fastener being substantially larger than the size of said at least one primary male fastener; (f) at least one secondary male fastener having a free floating outer end laterally extended from said edge of said first side panel, and an opposite inner end attached to said first side panel at a location adjacent to said at least one primary male fastener, such that its hook type mating surface is facing the same direction as the hook type mating surface of said at least one primary male fastener; and (g) said at least one secondary male fastener being substantially thinner than said edge of said first side panel; (h) whereby when said at least one primary male fastener is closed onto said at least one female fastener to close said diapering garment, said at least one secondary male fastener can also be closed onto said at least one female fastener to enforce the closure of said at least one primary male fastener.

Defined further alternatively, the present invention is a diapering garment, comprising: (a) a main diapering piece having an interior surface and an exterior surface; (b) said main diapering piece further having a closed side opening, and an opposite split side opening defined by the edges of a first and a second side panels; (c) at least one primary female fastener fully attached onto said interior surface of said main diapering piece, and located adjacent to said edge of said first side panel, such that its loop type mating surface is facing away from said interior surface of said main diapering piece; (d) at least one male fastener fully attached onto said exterior surface of said main diapering piece, and located adjacent to said edge of said second side panel, such that its hook type mating surface is facing away from said exterior surface of said main diapering piece; (e) the size of said at least one male fastener being substantially larger than the size of said at least one female primary fastener; (f) at least one secondary female fastener having a free floating outer end laterally extended from said edge of said first side panel, and an opposite inner end attached to said first side panel at a location adjacent to said at least one primary female fastener, such that its loop type mating surface is facing the same direction as the loop type mating surface of said at least one primary female fastener; and (g) said at least one secondary female fastener being substantially thinner than said edge of said first side panel; (h) whereby when said at least one primary female fastener is closed onto said at least one male fastener to close said diapering garment, said at least one secondary female fastener can also be closed onto said at least one male fastener to enforce the closure of said at least one primary female fastener.

Defined broadly, the present invention is a diapering garment, comprising: (a) a main diapering piece having a contoured edge; (b) at least one primary male fastener fully attached to said main diapering piece adjacent to said contoured edge, such that its hook type mating surface is facing away from said main diapering piece; (c) at least one female fastener fully attached to said main diapering piece adjacent to said contoured edge, and remote from said at least one primary male fastener, such that its loop type mating surface is facing away from said main diapering piece; (d) at least one secondary male fastener having a free floating outer end laterally extended from said contoured edge of said main diapering piece, and an opposite inner end attached to said main diapering piece adjacent to said at least one primary male fastener, such that its hook type mating surface is facing the same direction as the hook type mating surface of said at least one primary male fasteners; (e) the size of said at least one female fastener being substantially larger than the size of said at least one primary male fastener; and (f) the thickness of said at least one secondary male fastener being substantially thinner than the thickness of said contoured edge of said main diapering piece; (g) whereby when said at least one primary male fastener is closed onto said at least one female fastener to close said diapering garment, said at least one secondary male fastener can also be closed onto said at least one female fastener to enforce the closure of said at least one primary male fastener.

Defined also broadly, the present invention is a diapering garment, comprising: (a) a main diapering piece having a contoured edge; (b) at least one primary female fastener fully attached to said main diapering piece adjacent to said contoured edge, such that its loop type mating surface is facing away from said main diapering piece; (c) at least one male fastener fully attached to said main diapering piece adjacent to said contoured edge, and remote from said at least one primary female fastener, such that its hook type mating surface is facing away from said main diapering piece; (d) at least one secondary female fastener having a free floating outer end laterally extended from said contoured edge of said main diapering piece, and an opposite inner end attached to said main diapering piece adjacent to said at least one primary female fastener, such that its loop type mating surface is facing the same direction as the loop type mating surface of said at least one primary female fasteners; (e) the size of said at least one male fastener being larger than the size of said at least one primary female fastener; and (f) the thickness of said at least one secondary female fastener being thinner than the thickness of said contoured edge of said main diapering piece; (g) whereby when said at least one primary female fastener is closed onto said at least one male fastener to close said diapering garment, said at least one secondary female fastener can also be closed onto said at least one male fastener to enforce the closure of said at least one primary female fastener.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A diapering garment, comprising:
   a. a generally hourglass shaped main diapering piece having an interior surface, an exterior surface and a circumferential edge;
   b. said main diapering piece further having a generally straight front end and a widened rear end with two arcuate shaped rear corners;
   c. two primary male fasteners fully attached onto said interior surface of said main diapering piece and each having a hook type mating surface, and respectively located at said two rear corners adjacent to said circumferential edge of said main diapering piece, the hook type mating surfaces facing away from said interior surface of said main diapering piece;
   d. an elongated female fastener fully attached onto said exterior surface of said main diapering piece and having a loop type mating surface, and located at said front end adjacent to said circumferential edge of said main diapering piece, the loop type mating surface facing away from said exterior surface of said main diapering piece;
   e. two secondary male fasteners each having a hook type mating surface and a backing which has a thickness of less than hundredth of an inch (1/100"), a free floating outer end laterally extended from said circumferential edge of said main diapering piece, and an opposite inner end attached to said main diapering piece at a location adjacent to a respective one of said two primary male fasteners respectively, the hook type mating surfaces of the two secondary male fasteners facing a respective same direction as the hook type mating surfaces of said two primary male fasteners; and
   f. said two secondary male fasteners being substantially thinner than said circumferential edge of said main diapering piece;
   g. whereby when said two primary male fasteners are closed onto said elongated female fastener to close said diapering garment, said two secondary male fasteners can also be closed onto said elongated female fastener to deter said two primary male fasteners from being undesirably opened.

2. The invention as defined in claim 1 wherein said inner ends of said two secondary male fasteners are attached to said interior surface of said main diapering piece.

3. The invention as defined in claim 1 wherein said inner ends of said two secondary male fasteners are attached to said exterior surface of said main diapering piece.

4. The invention as defined in claim 1 wherein said inner ends of said two secondary male fasteners are attached to said circumferential edge of said main diapering piece.

5. The invention as defined in claim 2 wherein said inner ends of said two secondary male fasteners are respectively located between said two primary male fasteners and said circumferential edge of said main diapering piece.

6. The invention as defined in claim 2 wherein said inner ends of said two secondary male fasteners are respectively located immediately next to said two primary male fasteners.

7. The invention as defined in claim 2 wherein said inner ends of said two secondary male fasteners are respectively located beneath said two primary male fasteners, between said two primary male fasteners and said interior surface of said main diapering piece.

8. The invention as defined in claim 6 wherein a secondary male fastener is immediately adjacent a respective one of said primary male fasteners is integrally formed as an unitary piece with said respective primary male fastener.

9. The invention as defined in claim 8 wherein said unitary piece of male fastener is generally L-shaped.

10. The invention as defined in claim 1 wherein each said primary male fastener has an upper half portion adjacent to said rear end of said main diapering piece and an lower half portion.

11. The invention as defined in claim 10 wherein each said primary male fastener is generally square shaped.

12. The invention as defined in claim 10 wherein each one of said primary male fasteners has a size and each one of said secondary male fasteners also has a size, and the size of each said secondary male fastener is approximately half of the size of each said primary male fastener.

13. The invention as defined in claim 12 wherein each said secondary male fastener is generally rectangular shaped.

14. The invention as defined in claim 12 wherein one of said two secondary male fasteners is aligned with said upper portion of one of said two primary male fasteners, and the other one of said two secondary male fasteners is aligned with said lower portion of the other one of said two primary male fasteners, such that said two secondary male fasteners are completely offset from each other.

15. The invention as defined in claim 12 wherein said two secondary male fasteners are partially offset from each other.

16. The invention as defined in claim 12 wherein said two secondary male fasteners are aligned with each other.

17. A diapering garment, comprising:
a. a main diapering piece having an interior surface and an exterior surface;
b. said main diapering piece further having a front side, back side and two lateral sides containing leg openings, one of the two lateral sides being inseparable between the front and back sides, the other one of the two lateral sides being separable into a first side panel and a second side panel each having an edge;
c. at least one primary male fastener fully attached onto said interior surface of said main diapering piece and having a hook type mating surface, and located adjacent to said edge of said first side panel, the hook type mating surface facing away from said interior surface of said main diapering piece;
d. at least one female fastener fully attached onto said exterior surface of said main diapering piece and having a loop type mating surface, and located adjacent to said edge of said second side panel, the loop type mating surface facing away from said exterior surface of said main diapering piece;
e. said at least one female fastener having a size and said at least one primary male fastener also having a size, the size of said at least one female fastener being substantially larger than the size of said at least one primary male fastener;
f. at least one secondary male fastener having a hook type mating surface and a backing which has a thickness of less than hundredth of an inch (1/100"), a free floating outer end laterally extended from said edge of said first side panel, and an opposite inner end attached to said first side panel at a location adjacent to said at least one primary male fastener, the hook type mating surface facing a same direction as the hook type mating surface of said at least one primary male fastener; and
g. said at least one secondary male fastener being substantially thinner than said edge of said first side panel;
h. whereby when said at least one primary male fastener is closed onto said at least one female fastener to close said diapering garment, said at least one secondary male fastener can also be closed onto said at least one female fastener to deter said at least one primary male fastener from being undesirably opened.

18. The invention as defined in claim 17 wherein said inner end of said at least one secondary male fastener is attached to said interior surface of said main diapering piece.

19. The invention as defined in claim 17 wherein said at least one secondary male fastener has a size which is approximately half of the size of said at least one primary male fastener.

20. The invention as defined in claim 17 wherein the size of said at least one female fastener is approximately twice of the size of said at least one primary male fastener.

21. A diapering garment, comprising:
a. a generally hourglass shaped main diapering piece having an interior surface, an exterior surface and a circumferential edge;
b. said main diapering piece further having a generally straight front end and a widened rear end with two arcuate shaped rear corners;
c. two primary female fasteners fully attached onto said interior surface of said main diapering piece and each having a loop type mating surface, and respectively located at said two rear corners adjacent to said circumferential edge of said main diapering piece, the loop type mating surfaces facing away from said interior surface of said main diapering piece;

d. an elongated male fastener fully attached onto said exterior surface of said main diapering piece and having a hook type mating surface, and located at said front end adjacent to said circumferential edge of said main diapering piece, the hook type mating surface facing away from said exterior surface of said main diapering piece;

e. two secondary female fasteners each having a loop type mating surface and a backing which has a thickness of less than hundredth of an inch (1/100"), a free floating outer end laterally extended from said circumferential edge of said main diapering piece, and an opposite inner end attached to said main diapering piece at a location adjacent to a respective one of said two primary female fasteners respectively, the loop type mating surfaces of the two secondary female fasteners facing a respective same direction as the loop type mating surfaces of said two primary female fasteners; and f. said two secondary female fasteners being substantially thinner than said circumferential edge of said main diapering piece;

g. whereby when said two primary female fasteners are closed onto said elongated male fastener to close said diapering garment, said two secondary female fasteners can also be closed onto said elongated male fastener to deter said two primary female fasteners from being undesirably opened.

22. The invention as defined in claim 21 wherein said inner ends of said two secondary female fasteners are attached to said interior surface of said main diapering piece.

23. The invention as defined in claim 21 wherein each said primary female fastener has an upper half portion adjacent to said rear end of said main diapering piece and a lower half portion.

24. The invention as defined in claim 23 wherein each one of said secondary female fasteners has a size and each one of said primary female fasteners also has a size, and the size of each said secondary female fastener is approximately half of the size of each said primary female fastener.

25. The invention as defined in claim 24 wherein one of said two secondary female fasteners is aligned with said upper portion of one of said two primary female fasteners, and the other one of said two secondary female fasteners is aligned with said lower portion of the other one of said two primary female fasteners, such that said two secondary female fasteners are completely offset from each other.

26. The invention as defined in claim 24 wherein said two secondary female fasteners are partially offset from each other.

27. The invention as defined in claim 24 wherein said two secondary female fasteners are aligned with each other.

28. A diapering garment, comprising:
a. a main diapering piece having an interior surface and an exterior surface;
b. said main diapering piece further having a front side, a back side and two lateral sides containing leg openings, one of the two lateral sides being inseparable between the front and back sides, the other one of the two lateral sides being separable into a first side panel and a second side panel each having an edge;

c. at least one primary female fastener fully attached onto said interior surface of said main diapering piece and having a loop type mating surface, and located adjacent to said edge of said first side panel, the loop type mating surface facing away from said interior surface of said main diapering piece;

d. at least one male fastener fully attached onto said exterior surface of said main diapering piece and having a hook type mating surface, and located adjacent to said edge of said second side panel, the hook type mating surface facing away from said exterior surface of said main diapering piece;

e. said at least one male fastener having a size and said at least one primary female fastener also having a size, the size of said at least one male fastener being substantially larger than the size of said at least one female primary fastener;

f. at least one secondary female fastener having a loop type mating surface and a backing which has a thickness of less than hundredth of an inch (1/100"), a free floating outer end laterally extended from said edge of said first side panel, and an opposite inner end attached to said first side panel at a location adjacent to said at least one primary female fastener, the loop type mating surface facing a same direction as the loop type mating surface of said at least one primary female fastener; and g. said at least one secondary female fastener being substantially thinner than said edge of said first side panel;

h. whereby when said at least one primary female fastener is closed onto said at least one male fastener to close said diapering garment, said at least one secondary female fastener can also be closed onto said at least one male fastener to deter said at least one primary female fastener from being undesirably opened.

29. The invention as defined in claim 28 wherein said inner end of said at least one secondary female fastener is attached to said interior surface of said main diapering piece.

30. The invention as defined in claim 28 wherein said at least one secondary female fastener has a size which is approximately half of the size of said at least one primary female fastener.

31. The invention as defined in claim 28 wherein the size of said at least one male fastener is approximately twice of the size of said at least one primary female fastener.

32. A diapering garment, comprising:
a. a main diapering piece having a contoured edge;
b. at least one primary male fastener fully attached to said main diapering piece adjacent to said contoured edge and having a hook type mating surface, the hook type mating surface facing away from said main diapering piece;
c. at least one female fastener fully attached to said main diapering piece adjacent to said contoured edge and having a loop type mating surface, and remote from said at least one primary male fastener, the loop type mating surface facing away from said main diapering piece;
d. at least one secondary male fastener having a hook type mating surface and a backing which has a thickness of less than hundredth of an inch (1/100"), a free floating outer end laterally extended from said contoured edge of said main diapering piece, and an opposite inner end attached to said main diapering piece adjacent to said at least one primary male fastener, the hook type mating surface facing a same direction as the hook type mating surface of said at least one primary male fastener;

e. said at least one female fastener having a size and said at least one primary male fastener also having a size, the size of said at least one female fastener being substantially larger than the size of said at least one primary male fastener; and f. said at least one secondary male fastener being substantially thinner than said contoured edge of said main diapering piece;

g. whereby when said at least one primary male fastener is closed onto said at least one female fastener to close said diapering garment, said at least one secondary male fastener can also be closed onto said at least one female fastener to deter said at least one primary male fastener from being undesirably opened.

33. The invention as defined in claim 32 wherein said at least one secondary male fastener is substantially smaller than said at least one primary male fastener.

34. A diapering garment, comprising:

a. a main diapering piece having a contoured edge;

b. at least one primary female fastener fully attached to said main diapering piece adjacent to said contoured edge and having a loop type mating surface, the hook type mating surface facing away from said main diapering piece;

c. at least one male fastener fully attached to said main diapering piece adjacent to said contoured edge and having a hook type mating surface, and remote from said at least one primary female fastener, the hook type mating surface facing away from said main diapering piece;

d. at least one secondary female fastener having a loop type mating surface and a backing which has a thickness of less than hundredth of an inch (1/100"), a free floating outer end laterally extended from said contoured edge of said main diapering piece, and an opposite inner end attached to said main diapering piece adjacent to said at least one primary female fastener, the loop type mating surface facing a same direction as the loop type mating surface of said at least one primary female fastener;

e. said at least one male fastener having a size and said at least one primary female fastener also having a size, the size of said at least one male fastener being larger than the size of said at least one primary female fastener; and f. said at least one secondary female fastener being substantially thinner than said contoured edge of said main diapering piece;

g. whereby when said at least one primary female fastener is closed onto said at least one male fastener to close said diapering garment, said at least one secondary female fastener can also be closed onto said at least one male fastener to deter said at least one primary female fastener from being undesirably opened.

35. The invention as defined in claim 34 wherein said at least one secondary female fastener is substantially smaller than said at least one primary female fastener.

* * * * *